(12) United States Patent
Liu et al.

(10) Patent No.: US 12,019,055 B2
(45) Date of Patent: Jun. 25, 2024

(54) CYCLIC DYNAMIC LOADING-CONFINING PRESSURE INSTANTANEOUS UNLOADING TEST DEVICE AND ITS APPLICATION METHOD

(71) Applicant: SHANDONG UNIVERSITY OF SCIENCE AND TECHNOLOGY, Qingdao (CN)

(72) Inventors: Xuesheng Liu, Qingdao (CN); Shenglong Yang, Qingdao (CN); Yunliang Tan, Qingdao (CN); Deyuan Fan, Qingdao (CN); Xuebin Li, Qingdao (CN); Hu Song, Qingdao (CN)

(73) Assignee: SHANDONG UNIVERSITY OF SCIENCE AND TECHNOLOGY, Qingdao (CN)

( * ) Notice: Subject to any disclaimer, the term of this patent is extended or adjusted under 35 U.S.C. 154(b) by 96 days.

(21) Appl. No.: 17/807,244

(22) Filed: Jun. 16, 2022

(65) Prior Publication Data

US 2023/0400397 A1    Dec. 14, 2023

(51) Int. Cl.
| | |
|---|---|
| *G01N 3/34* | (2006.01) |
| *G01N 3/04* | (2006.01) |
| *G01N 3/38* | (2006.01) |
| *G01N 33/24* | (2006.01) |

(52) U.S. Cl.
CPC ............... *G01N 3/34* (2013.01); *G01N 33/24* (2013.01); *G01N 2203/0005* (2013.01); *G01N 2203/0252* (2013.01)

(58) Field of Classification Search
CPC ............ G01N 29/14; G01N 7/04; G01N 3/00; G01N 3/04; G01N 3/34; G01N 3/10; G01N 33/24; G01N 3/52; G01N 3/20; G01N 1/08; G01N 3/14; G01N 3/60; G01N 15/0826; G01N 3/307; G01N 3/064; G01N 3/24; G01N 3/08; G01N 3/32; G01N 23/046; G01N 3/18; G01N 3/38; G01N 3/12; G01N 3/36; G01N 3/02; G01N 15/08; G01M 13/021; G01M 7/027; G06F 30/20; G06F 30/13; E02D 33/00; Y02P 90/02; Y02E 30/30; F04B 43/067
See application file for complete search history.

(56) References Cited

U.S. PATENT DOCUMENTS

2022/0128442 A1\*    4/2022   Zhou ...................... G01N 3/317

\* cited by examiner

*Primary Examiner* — Brandi N Hopkins
(74) *Attorney, Agent, or Firm* — CBM PATENT CONSULTING, LLC

(57) ABSTRACT

A cyclic dynamic loading-confining pressure instantaneous unloading test device includes a load-supporting frame system, a cyclic dynamic loading system, a confining pressure loading system, a monitoring system, a control system and a data analysis system; the top of the load-supporting frame system is equipped with the cyclic dynamic loading system, the cyclic dynamic loading system is connected with the control system, the bottom of the load-supporting frame system is equipped with the confining pressure loading system, the cyclic dynamic loading system and the confining pressure loading system are equipped with the monitoring system, the monitoring system and the control system are connected with the data analysis system.

10 Claims, 5 Drawing Sheets

CYCLIC DYNAMIC LOADING-CONFINING PRESSURE INSTANTANEOUS UNLOADING TEST DEVICE AND ITS APPLICATION METHOD

CROSS REFERENCES

This application claims priority to Chinese Patent Application Ser. No. CN2022105601470 filed on 23 May 2022.

TECHNICAL FIELD

The invention relates to a cyclic dynamic loading-confining pressure instantaneous unloading test device and its application method, which belongs to the technical field of rock mechanics test device.

BACKGROUND TECHNOLOGY

In the process of coal mining, coal seam is often affected by cyclic dynamic load, such as geological structural movement, excavation and support of roadway, periodic roof pressure, extrusion of blasting stress wave on coal seam, and the effect of support fluctuating on top coal. The mechanical properties of coal seam under cyclic dynamic loading disturbance are one of the important factors affecting coal mine safety production. In the actual production process, the space-time relationship of mining caused by coal mining is constantly changing, which leads to the redistribution of surrounding rock stress, resulting in the loading of coal is multiple cycles, such as the coal pillars of setting up, roadway surrounding rock affected by multiple mining. Coal underground mining often produces periodic disturbance to coal and rock surround around mining area. Studying the deformation and failure characteristics of coal (rock) under cyclic loading conditions is helpful to understand the mechanism of coal (rock) damage, degradation and instability destruction, and provide effective analysis methods for obtaining coal (rock) instability precursors. At the same time, in the actual production process, when the coal (rock) is unstable, the impact force caused by the instability and expansion of coal (rock) makes the roadway support method instantaneous failure, and the surrounding rock is damaged by the impact. Therefore, in order to study the mechanical conditions of surrounding rock under the actual conditions of underground roadway, it is necessary to consider the mechanical properties of coal seam under cyclic dynamic loading disturbance and confining pressure instantaneous unloading.

At present, two test methods are generally used to study the mechanical properties of coal (rock) under cyclic dynamic loading in the laboratory. One is to apply cyclic dynamic loading through hydraulic cylinder system. China patent CN112986026A provides a high-frequency and high-load cyclic dynamic loading test device and test method for rock, which can provide high-frequency, high-load and stepless adjustable cyclic dynamic loading for rock test. The cyclic dynamic loading is to use the ball screw to drive the piston pump to adjust the flow of oil into the dynamic loading cylinder, thus driving the piston rod of the cylinder to impose cyclic dynamic loading on the coal (rock) sample. However, the cushion performance of ball screw is very low and there is wear, which will affect the positioning accuracy due to friction, thus affecting the flow of oil into the cylinder, resulting in low accuracy of applying cyclic dynamic loading, which has a great influence on the experimental results. At the same time, the hydraulic oil is easy to leak and cause safety influence. China patent CN112986026A provides a rock mechanics test machine and test method of variable frequency and variable strength static-dynamic coupling loading. The device can improve the cyclic dynamic loading of rock samples. The cyclic dynamic loading is achieved by the meshing movement of the impact screw and the thread of the asymmetric gear, thus driving the loading chassis to do axial harmonic motion and realize the dynamic loading application of rock samples. However, the device does not consider the confining pressure of rock samples, and the test range is small.

Another test method in the existing technology is to use the split Hopkinson pressure bar (SHPB) system to carry out multiple cyclic loading on the samples, and use the Hopkinson pressure bar to test the compressive stress of the samples. However, it is interval and independent to use this device to carry out cyclic dynamic loading test, and continuous cyclic test cannot be carried out.

Invention Content

In view of the shortcomings of the existing technology, the invention provides a cyclic dynamic loading-confining pressure instantaneous unloading test device with simple operation and high test accuracy. When the specimen is subjected to expansion failure, the instantaneous unloading pressure of the specimen is realized, which is highly similar to the actual conditions of the surrounding rock of the underground roadway, and the test results are reliable.

The invention also provides the application method of the above cyclic dynamic loading-confining pressure instantaneous unloading test device.

The technical scheme of the invention is as follows:

A cyclic dynamic loading-confining pressure instantaneous unloading test device includes a load-supporting frame system, a cyclic dynamic loading system, a confining pressure loading system, a monitoring system, a control system and a data analysis system.

The top of the load-supporting frame system is equipped with the cyclic dynamic loading system, the cyclic dynamic loading system is connected with the control system, the bottom of the load-supporting frame system is equipped with the confining pressure loading system, the cyclic dynamic loading system and the confining pressure loading system are equipped with the monitoring system, the monitoring system and the control system are connected with the data analysis system.

Cyclic dynamic loading system is used to apply top-down axial cyclic load on the specimen;

Confining pressure loading system for radial confining pressure loading on the specimen;

The monitoring system is used to monitor the force, deformation and failure of the specimen during loading and unloading;

A control system for controlling the cyclic loading system;

The data analysis system is connected with the monitoring system and the control system to receive and analyze the data of the monitoring system.

Optimally, the load-supporting frame system includes the base plate, the operating platform, the column and the roof. The upper surface of the base plate is equipped with the operating platform, and the confining pressure loading system is set on the operating platform. The roof is fixed through the column above the base plate, and the cyclic dynamic loading system is set below the roof.

Optimally, the cyclic dynamic loading system includes servo motor, rotary shaft, rotary wheel, cam wheel, first connecting rod, second connecting rod and heavy hammer.

The servo motor is horizontally fixed in the load-supporting frame system. The output shaft of the servo motor is connected with the rotary wheel through the rotary shaft. The arc groove is uniformly set on the rotary wheel. The cam wheel is set on the lower side of the rotary wheel. The cam wheel is connected with the first connecting rod through the connecting shaft. The lower side of the first connecting rod is connected with the heavy hammer through the second connecting rod. The second connecting rod is elastically fixed on the top of the load-supporting frame system through the four vertical holding devices with circumferential uniform setting.

The control system controls the servo motor to drive the rotation of the rotary shaft, and the rotary wheel rotates with the help of the rotary shaft. The rotary wheel is irregular circular. The salient of the rotary wheel contacts with the cam wheel and drives the cam wheel to move vertically downward, so the heavy hammer is driven to move vertically downward by the first connecting rod and the second connecting rod. When the cam wheel is rotated to the bottom of the rotary wheel arc groove, the vertical holding device drives the cam wheel to move vertically upward under the spring elastic force, the cam wheel contacts with the rotary wheel and completes a dynamic load application. The vertical holding device makes the heavy hammer move up and down while maintaining the vertical state, and the force on the specimen is more uniform. Controlling the output speed of the rotary shaft can realize the cyclic load application with different cyclic amplitudes and different load intensities; the rotary wheel with uniform or non-uniform rotation is made by means of the rotary shaft, and each rotation is independent for one week, which can realize the rotation of different rates and accelerations.

In further optimization, the vertical holding device is L-shaped rod, and the top of the vertical holding device is fixed to the load-supporting frame system through the spring. The L-shaped rod can work better with the spring.

Optimally, there are at least two arc grooves on the rotary wheel. By changing the number of arc grooves, different times of loading can be applied in a week.

Optimally, the second connecting rod is connected with the heavy hammer threaded connections, and the cyclic loading with different load intensities can be achieved by replacing the heavy hammers with different weights.

Optimally, the confining pressure loading system includes the first arc confining pressure plate, the second arc confining pressure plate, the third arc confining pressure plate and the fourth arc confining pressure plate. The first arc confining pressure plate and the second arc confining pressure plate are connected by bolts. The second arc confining pressure plate is connected with the fourth arc confining pressure plate through the first hinge. The fourth arc confining pressure plate is connected with the third arc confining pressure plate through the second hinge. The third arc confining pressure plate is connected with the first arc confining pressure plate through the third hinge.

Optimally, the monitoring system includes the first force sensor, the second force sensor, the displacement sensor and the acoustic emission sensor. The first force sensor is set on the heavy hammer, and the second force sensor, the displacement sensor and the acoustic emission sensor are set on the surface of the specimen in the confining pressure loading system. The first force sensor, the second force sensor, the displacement sensor and the acoustic emission sensor are connected with the data analysis system through the signal collector.

The procedures for the use of the cyclic dynamic loading-confining pressure instantaneous unloading test device are as follows:

Step 1: Making cylindrical specimens;

Step 2: The specimen is fixed at the middle position of the operating platform surface, and then the confining pressure loading system is placed around the specimen along the radial direction of the specimen, and the confining pressure loading system is applied to the specimen;

Step 3: According to the load strength of the test requirements, determine the heavy hammer that meets the test requirements, adjust the speed of the servo motor, apply the cyclic loading of the target load strength to the specimen;

Step 4: The specimen is subjected to expansion failure under cyclic dynamic loading. The confining pressure loading system is subjected to expansion of the specimen and generates outward force. The hinge is subjected to tensile failure. The confining pressure loading system loses contact with the specimen and the specimen instantaneously unloads the confining pressure;

Step 5: The data analysis system processes and analyzes the data from the monitoring system to obtain the stress, strain curve and acoustic emission energy curve of the specimen, and analyzes the mechanical characteristics of the specimen before and after the confining pressure instantaneous unloading.

In further optimization, in the step 2, when the confining pressure loading system is applied to the specimen, according to the test requirements, the numerical torque wrench is used to tighten the bolt, and the confining pressure of the target strength is applied to the specimen.

Optimally, in the step 4, when the specimen occurs expansion failure in the horizontal direction of the bolt and the second hinge, the first hinge and the third hinge are damaged by tension, the confining pressure loading system loses contact with the specimen, and the specimen releases the confining pressure instantaneously; when the specimen occurs expansion failure in the horizontal direction of the first and third hinges, the second hinge is damaged by tension, and the confining pressure loading system loses contact with the specimen, and the specimen releases the confining pressure instantaneously.

The Beneficial Effect of the Invention is:

1. The invention has the advantages of simple operation and high test accuracy. When the specimen is damaged by expansion, the confining pressure instantaneous unloading of the specimen is realized. The confining pressure is applied passively. The confining pressure is proportional to the expansion deformation of the specimen and the ratio can be adjusted. The maximum confining pressure can be set in advance. When the confining pressure exceeds the set value, the confining pressure can be instantaneously reduced to zero. The loading and unloading conditions of the confining pressure are similar to the actual conditions of the surrounding rock of the underground roadway, and the test results are reliable.

2. The invention adopts the combination of rotary wheel and cam wheel, and uses the vertical holding device to hold the heavy hammer, so that the heavy hammer moves up and down while maintaining a vertical state. The force acting on the specimen is more uniform, so that the structure tends to be stable, and the stability of the load is also guaranteed.

3. According to the load strength required by the test, the invention can select the heavy hammer that meets the test requirements, and realize the cyclic dynamic loading of applying the target load strength to the specimen by adjusting the rotational speed of the servo motor required by the test.

4. According to the design of the test scheme, different rotary wheel, heavy hammer and confining pressure loading systems can be selected. The device has high replaceability, simple structure and convenient operation.

In these figures: 1—load-supporting frame system, 11—base plate, 12—operating platform, 13—column, 14—roof;
2—cyclic dynamic loading system, 21—servo motor, 22—rotary shaft, 23—keyway, 24—rotary wheel, 25—cam wheel, 26—connecting shaft, 27—first connecting rod, 28—second connecting rod, 29—heavy hammer, 210—vertical holding device;
3—confining pressure loading system, 31—the first arc confining pressure plate, 32—the second arc confining pressure plate, 33—the third arc confining pressure plate, 34—the fourth arc confining pressure plate, 35—screw hole, 36—bolt, 37—the first hinge, 38—the second hinge, 39—the third hinge;
4—monitoring system, 41—the first force sensor, 42—second force sensor, 43—displacement sensor, 44—acoustic emission sensor, 45—signal collector;
5—control system;
6—data analysis system;
7—specimen.

DETAILED EMBODIMENTS

In the following, the invention is further explained by the implementation example and the attached figure, but not limited to this.

Embodiment 1

Figure 1:
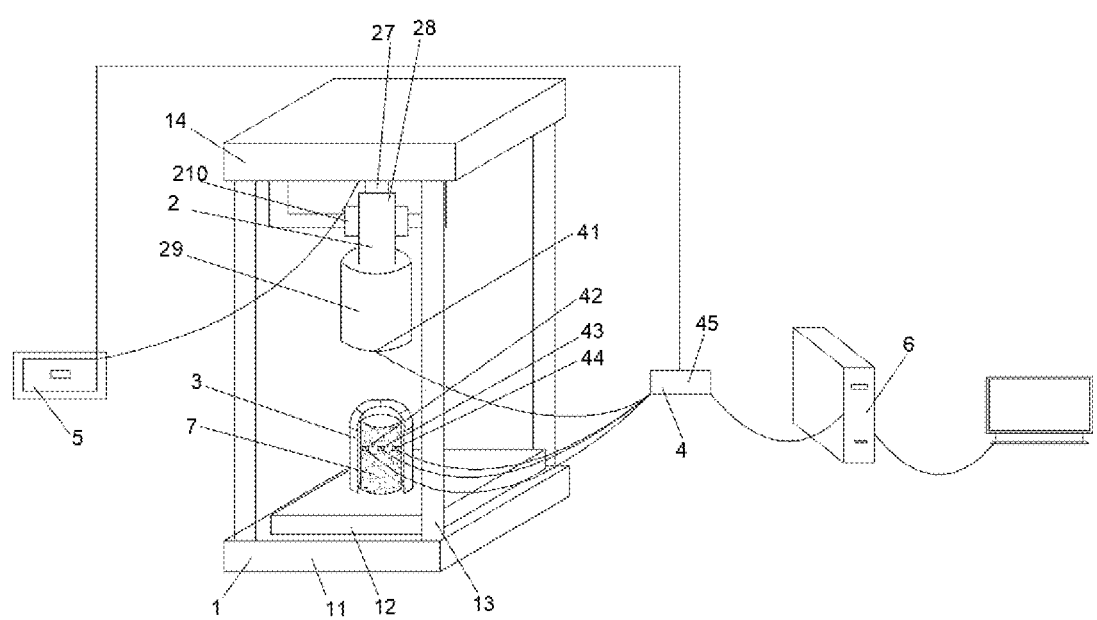
FIG. 1 is the structural diagram of the invention.
Figure 2:
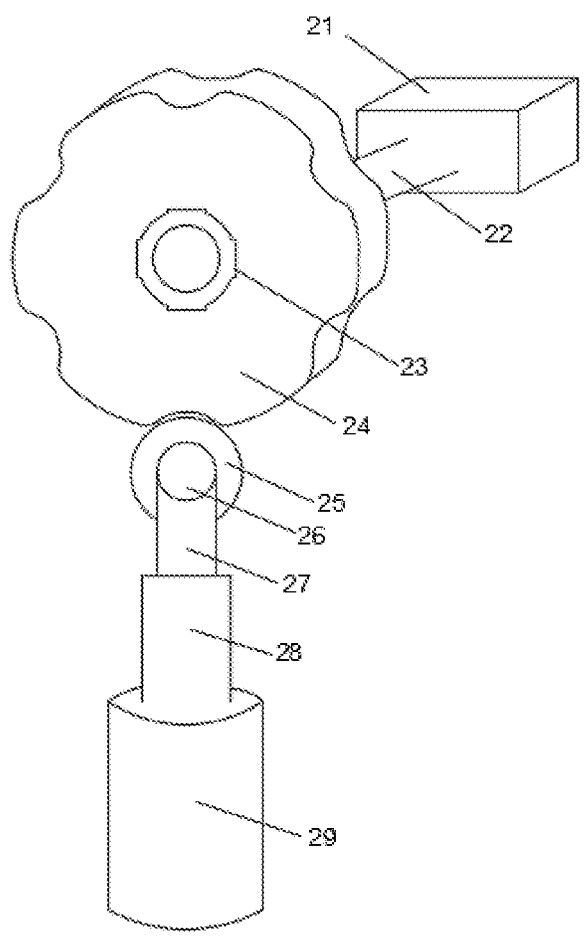
FIG. 2 is the structural diagram of the cyclic dynamic loading system of the invention.
Figure 3:
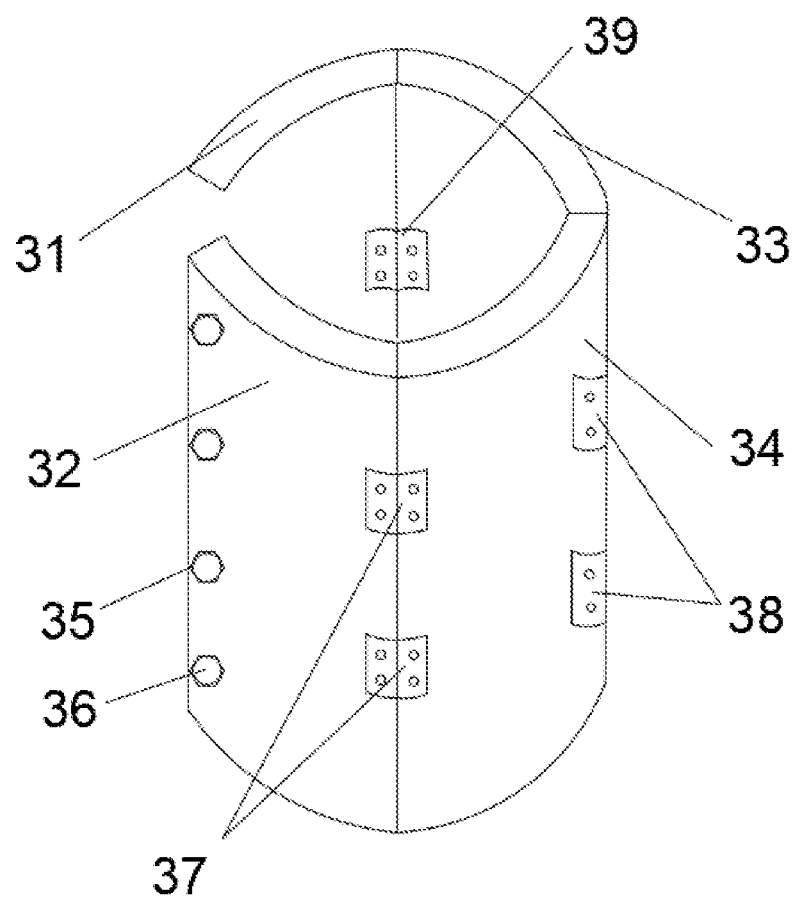
FIG. 3 is the structural diagram of the confining pressure loading system of the invention.
Figure 4:
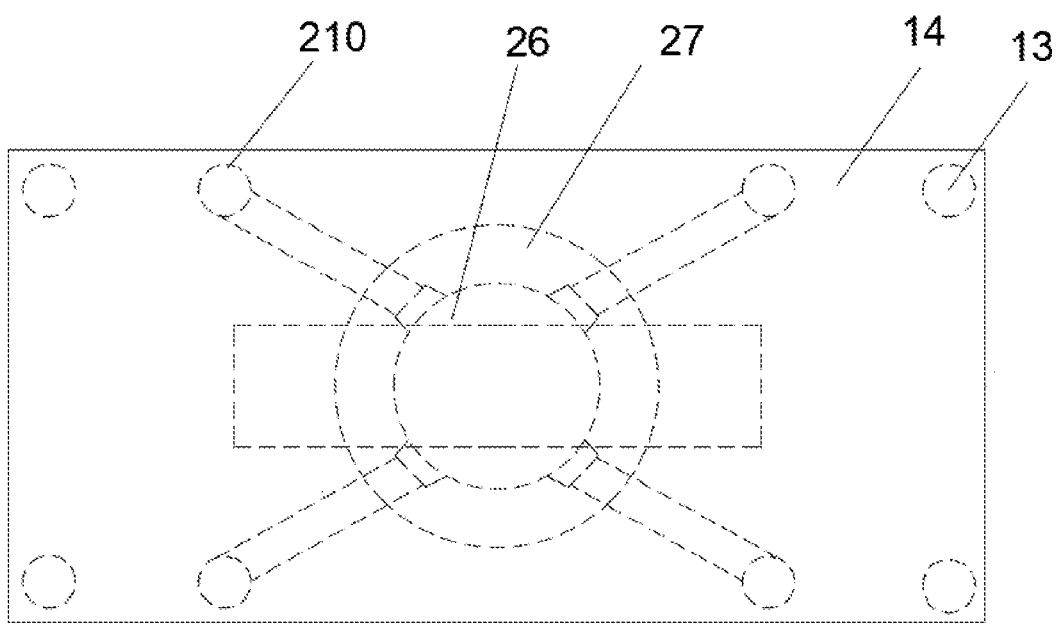
FIG. 4 is the schematic diagram of the installation position of the vertical holding device in the invention.
Figure 5:
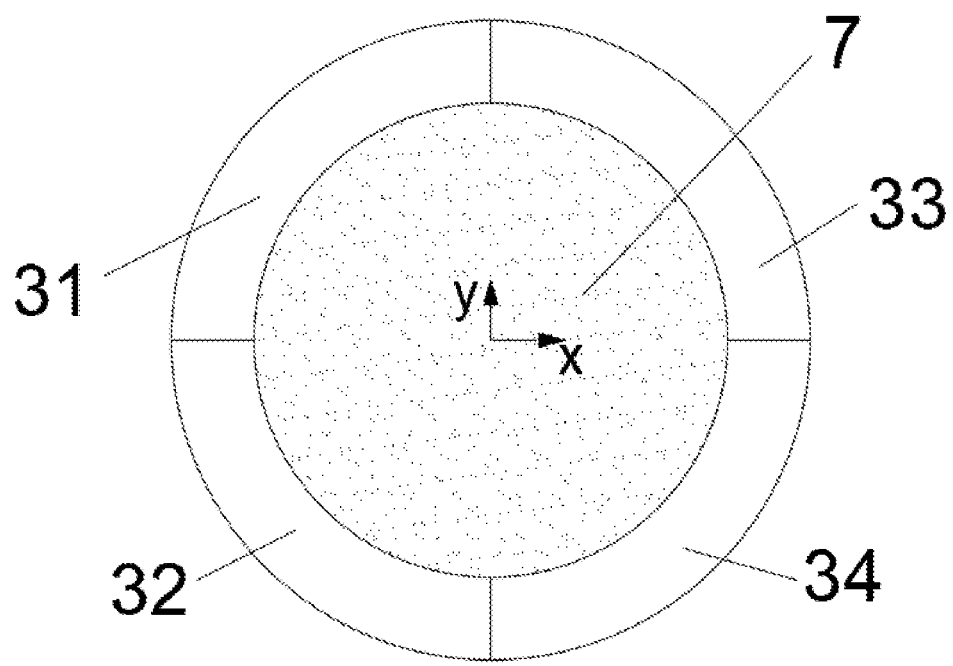
FIG. 5 is the schematic diagram of the relative position of the specimen in the invention.

As shown in FIGS. 1-5, the embodiment provides a cyclic dynamic loading-confining pressure instantaneous unloading test device, including load-supporting frame system 1, cyclic dynamic loading system 2, confining pressure loading system 3, monitoring system 4, control system 5 and data analysis system 6.

The top of the load-supporting frame system 1 is equipped with the cyclic dynamic loading system 2, the cyclic dynamic loading system 2 is connected with the control system 5, the bottom of the load-supporting frame system 1 is equipped with the confining pressure loading system 3, the cyclic dynamic loading system 2 and the confining pressure loading system 3 are equipped with the monitoring system 4, the monitoring system 4 and the control system 2 are connected with the data analysis system 6.

Cyclic dynamic loading system 2 is used to apply top-down axial cyclic loading on the specimen;

Confining pressure loading system 3 for radial confining pressure loading on the specimen;

The monitoring system 4 is used to monitor the force, deformation and failure of the specimen during loading and unloading;

A control system 5 for controlling the cyclic loading system;

The data analysis system 6 is connected with the monitoring system and the control system to receive and analyze the data of the monitoring system.

The load-supporting frame system 1 includes the base plate 11, the operating platform 12, the column 13 and the roof 14. The upper surface of the base plate 11 is equipped with the operating platform 12, and the confining pressure loading system 3 is set on the operating platform 12. The roof 14 is fixed through the column 13 above the base plate 11, and the cyclic dynamic loading system 2 is set below the roof 14.

The cyclic dynamic loading system 2 includes servo motor 21, rotary shaft 22, rotary wheel 24, cam wheel 25, first connecting rod 27, second connecting rod 28 and heavy hammer 29. The servo motor 21 is horizontally fixed in the load-supporting frame system 1. The output shaft of servo motor 21 is connected to the keyway 23 on the rotary wheel 24 through the shaft 22. The arc groove is uniformly set on the rotary wheel 24. The cam wheel 25 is set on the lower side of the rotary wheel 24. The cam wheel 25 is connected to the first connecting rod 27 through the connecting shaft 26. The lower side of the first connecting rod 27 is connected with the heavy hammer 29 through the second connecting rod 28. The second connecting rod 28 is elastically fixed on the top of the load-supporting frame system 1 through the four vertical holding devices 210 with circumferential uniform setting. First connecting rod 27, second connecting rod 28, heavy hammer 29, specimen 7 concentric arrangement.

The control system 5 controls the servo motor 21 to drive the rotation of the rotary shaft 22, and the rotary wheel 24 rotates with the help of the rotary shaft 22. The rotary wheel 24 is irregular circular. The salient of the rotary wheel 24 contacts with the cam wheel 25 and drives the cam wheel 25 to move vertically downward, so the heavy hammer 29 is driven to move vertically downward by the first connecting rod 27 and the second connecting rod 28. When the cam wheel 25 is rotated to the bottom of the rotary wheel 24 arc groove, the vertical holding device 210 drives the cam wheel 25 to move vertically upward under the spring elastic force, the cam wheel 25 contacts with the rotary wheel 24 and completes a dynamic load application. The vertical holding device 210 makes the heavy hammer 29 move up and down while maintaining the vertical state, and the force on the specimen 7 is more uniform. Controlling the output speed of the rotary shaft 22 can realize the cyclic load application with different cyclic amplitudes and different load intensities; the rotary wheel with uniform or non-uniform rotation is made by means of the rotary shaft, and each rotation is independent for one week, which can realize the rotation of different rates and accelerations.

The vertical holding device 210 is L-shaped rod, and the top of the vertical holding device 210 is fixed to the load-supporting frame system 1 through the spring. The L-shaped rod can work better with the spring.

There are six arc grooves on the rotary wheel 24. By changing the number of arc grooves, the loading of different times in a week can be applied.

The confining pressure loading system 3 includes the first arc confining pressure plate 31, the second arc confining pressure plate 32, the third arc confining pressure plate 33 and the fourth arc confining pressure plate 34. Screw holes 35 set on the first arc pressure plate 31 and the second arc pressure plate 32. The first arc confining pressure plate 31 and the second arc confining pressure plate 32 are connected by bolts 36. The second arc confining pressure plate 32 is connected with the fourth arc confining pressure plate 34 through the first hinge 37. The fourth arc confining pressure plate 34 is connected with the third arc confining pressure plate 33 through the second hinge 38. The third arc confining pressure plate 33 is connected with the first arc confining pressure plate 31 through the third hinge 39.

The monitoring system 4 includes the first force sensor 41, the second force sensor 42, the displacement sensor 43 and the acoustic emission sensor 44. The first force sensor 41 is set on the heavy hammer 29, and the second force sensor 42, the displacement sensor 43 and the acoustic emission sensor 44 are set on the surface of the specimen 7 in the confining pressure loading system 3. The first force sensor 41, the second force sensor 42, the displacement sensor 43 and the acoustic emission sensor 44 are connected with the data analysis system 6 through the signal collector 45.

The procedures for the use of the cyclic dynamic loading-confining pressure instantaneous unloading test device are as follows:

Step 1: Making cylindrical specimens;

Step 2: The specimen 7 is fixed at the middle position of the operating platform 12 surface, and then the confining pressure loading system 3 is placed around the specimen 7 along the radial direction of the specimen 7, and the confining pressure loading system 3 is applied to the specimen 7;

Step 3: According to the load strength of the test requirements, determine the heavy hammer 29 that meets the test requirements, adjust the speed of the servo motor 21, apply the cyclic loading of the target load strength to the specimen 7;

Step 4: The specimen 7 is subjected to expansion failure under cyclic dynamic loading. The confining pressure loading system 3 is subjected to expansion of the specimen and generates outward force. The hinge is subjected to tensile failure. The confining pressure loading system 3 loses contact with the specimen 7 and the specimen 7 instantaneously unloads the confining pressure;

Step 5: The data analysis system 6 processes and analyzes the data from the monitoring system 4 to obtain the stress, strain curve and acoustic emission energy curve of the specimen, and analyzes the mechanical characteristics of the specimen 7 before and after the confining pressure instantaneous unloading.

Embodiment 2

A cyclic dynamic loading-confining pressure instantaneous unloading test device, as described in embodiment 1. The difference is that there are two arc grooves on the rotary wheel 24, the second connecting rod 28 is connected with the heavy hammer 29 threaded connections. By replacing the heavy hammers with different weights, the cyclic loading can be applied with different load strength.

Embodiment 3

A method of using a cyclic dynamic loading-confining pressure instantaneous unloading test device, the steps are described in embodiment 1. The difference is that in the step 2, when the confining pressure loading system 3 is applied to the specimen 7, according to the test requirements, the numerical torque wrench is used to tighten the bolt, and the confining pressure of the target strength is applied to the specimen.

Embodiment 4

A method of using a cyclic dynamic loading-confining pressure instantaneous unloading test device, the steps are described in embodiment 1. The difference is that in the step 4, when the specimen 7 occurs expansion failure in the horizontal direction of the bolt and the second hinge, the first hinge 37 and the third hinge 39 are damaged by tension, the confining pressure loading system 3 loses contact with the specimen 7, and the specimen 7 releases the confining pressure instantaneously; when the specimen 7 occurs expansion failure in the horizontal direction of the first and third hinges, the second hinge 38 is damaged by tension, and the confining pressure loading system 3 loses contact with the specimen 7, and the specimen 7 releases the confining pressure instantaneously.

As mentioned above, only the detailed embodiments of the invention, but the protection scope of the invention is not limited to this, any change or replacement that is not thought of by creative labor should be covered in the protection scope of the invention. Therefore, the protection scope of the invention should be based on the protection scope limited by the claims.

What is claimed is:

1. A cyclic dynamic loading-confining pressure instantaneous unloading test device comprising
   a load-supporting frame system for operating loading,
   a cyclic dynamic loading system for performing a top-down axial cyclic loading,
   a confining pressure loading system for performing a radial confining pressure loading,
   a monitoring system for monitoring force, deformation and specimen failure,
   a control system for controlling the cyclic dynamic loading system and
   a data analysis system for analyzing data from the monitoring system; wherein
      a top of the load-supporting frame system is installed by the cyclic dynamic loading system, the cyclic dynamic loading system is provided with the control system, the bottom of the load-supporting frame system is installed by the confining pressure loading system, the cyclic dynamic loading system and the confining pressure loading system are installed by the monitoring system, the monitoring system and the control system are provided with the data analysis system;
   the confining pressure loading system comprises a first arc confining pressure plate, a second arc confining pressure plate, a third arc confining pressure plate and a fourth arc confining pressure plate; wherein
   the first arc confining pressure plate and the second arc confining pressure plate are installed by bolts; the second arc confining pressure plate is provided with the fourth arc confining pressure plate through a first hinge; the fourth arc confining pressure plate is provided with the third arc confining pressure plate through a second hinge; the third arc confining pressure plate is provided with the first arc confining pressure plate through a third hinge.

2. The cyclic dynamic loading-confining pressure instantaneous unloading test device according to claim 1, wherein the load-supporting frame system comprises a base plate, an operating platform, a column and a roof; wherein
an upper surface of the base plate is equipped with the operating platform, and the confining pressure loading system is set on the operating platform; the roof is fixed through the column above the base plate, and the cyclic dynamic loading system is set below the roof.

3. The cyclic dynamic loading-confining pressure instantaneous unloading test device according to claim 2, wherein the cyclic dynamic loading system comprises a servo motor, a rotary shaft, a rotary wheel, a cam wheel, a first connecting rod, a second connecting rod and a heavy hammer; wherein
the servo motor is horizontally fixed in the load-supporting frame system; an output shaft of the servo motor is connected with the rotary wheel through the rotary shaft; arc grooves are uniformly set on the rotary wheel; the cam wheel is set on a lower side of the rotary wheel; the cam wheel is connected with the first connecting rod through a connecting shaft; a lower side of the first connecting rod is connected with the heavy hammer through the second connecting rod; the second connecting rod is elastically fixed on a top of the load-supporting frame system through the four vertical holding device with circumferential uniform setting.

4. The cyclic dynamic loading-confining pressure instantaneous unloading test device according to claim 3, wherein each of the four vertical holding devices is L-shaped rod, and a top of the vertical holding device is fixed to the load-supporting frame system through a spring.

5. The cyclic dynamic loading-confining pressure instantaneous unloading test device according to claim 3, wherein there are at least two arc grooves on the rotary wheel, and the second connecting rod is connected with heavy hammer threaded connections.

6. The cyclic dynamic loading-confining pressure instantaneous unloading test device according to claim 4, wherein the monitoring system comprises a first force sensor, a second force sensor, a displacement sensor and an acoustic emission sensor; wherein
the first force sensor is set on the heavy hammer, and the second force sensor, the displacement sensor and the acoustic emission sensor are set on surface of a specimen in the confining pressure loading system; the first force sensor, the second force sensor, the displacement sensor and the acoustic emission sensor are connected with the data analysis system through a signal collector.

7. A method for performing the cyclic dynamic loading-confining pressure instantaneous unloading test device according to claim 6 comprising the following steps:
step i: making cylindrical specimens;
step ii: the specimen is fixed at a middle position of an operating platform surface, and then the confining pressure loading system is placed around the specimen along a radial direction of the specimen, and the confining pressure loading system is applied to the specimen;
step iii: according to the load strength of the test requirements, determining the heavy hammer that meets the test requirements, adjusting the speed of the servo motor, apply the cyclic loading of the target load strength to the specimen;
step iv: the specimen is subjected to expansion failure under cyclic dynamic loading; the confining pressure loading system is subjected to expansion of the specimen and generates outward force; the hinge is subjected to tensile failure; the confining pressure loading system loses contact with the specimen and the specimen instantaneously unloads the confining pressure; and
step v: the data analysis system processes and analyzes the data from the monitoring system to obtain the stress, strain curve and acoustic emission energy curve of the specimen, and analyzes the mechanical characteristics of the specimen before and after the instantaneous unloading the confining pressure.

8. The use method for performing the cyclic dynamic loading-confining pressure instantaneous unloading test device according to claim 7, wherein in the step ii,
when the confining pressure loading system is applied to the specimen, according to the test requirements, a numerical torque wrench is used to tighten the bolt, and the confining pressure of the target strength is applied to the specimen.

9. The use method for performing the cyclic dynamic loading-confining pressure instantaneous unloading test device according to claim 7, wherein in the step iii,
the cyclic loading process comprises the control system controlling the servo motor to drive the rotary shaft, and the rotary wheel rotating with the rotary shaft; the rotary wheel is irregular circular; a salient of the rotary wheel contacts with the cam wheel and drives the cam wheel to move vertically downward, se and the heavy hammer is driven to move vertically downward by the first connecting rod and the second connecting rod;
when the cam wheel is rotated to a bottom of the rotary wheel arc groove, the vertical holding device drives the cam wheel to move vertically upward under a spring elastic force, the cam wheel contacts with the rotary wheel and completes a dynamic load application; the cyclic load is applied under the rotation of the rotary wheel.

10. The method for performing the cyclic dynamic loading-confining pressure instantaneous unloading test device according to claim 7, wherein in the step iv,
when the specimen occurs expansion failure in the horizontal direction of the bolt and the second hinge, the first hinge and the third hinge are damaged by tension, the confining pressure loading system loses contact with the specimen, and the specimen releases the confining pressure instantaneously; and
when the specimen occurs expansion failure in the horizontal direction of the first and third hinges, the second hinge is damaged by tension, and the confining pressure loading system loses contact with the specimen, and the specimen releases the confining pressure instantaneously.

\* \* \* \* \*